United States Patent
Giusti et al.

(10) Patent No.: US 10,941,880 B2
(45) Date of Patent: Mar. 9, 2021

(54) PIEZOELECTRIC VALVE MODULE, METHOD FOR MANUFACTURING THE VALVE MODULE, METHOD FOR OPERATING THE VALVE MODULE, AND RESPIRATORY AID DEVICE INCLUDING ONE OR MORE OF THE VALVE MODULES

(71) Applicant: STMicroelectronics S.r.l., Agrate Brianza (IT)

(72) Inventors: Domenico Giusti, Monza (IT); Oriana Rita Antonia Di Marco, Milan (IT); Igor Varisco, Settimo Milanese (IT)

(73) Assignee: STMicroelectronics S.r.l., Agrate Brianza (IT)

(*) Notice: Subject to any disclaimer, the term of this patent is extended or adjusted under 35 U.S.C. 154(b) by 20 days.

(21) Appl. No.: 16/295,410

(22) Filed: Mar. 7, 2019

(65) Prior Publication Data

US 2019/0285196 A1 Sep. 19, 2019

(30) Foreign Application Priority Data

Mar. 14, 2018 (IT) .................. 102018000003552

(51) Int. Cl.
*F16K 99/00* (2006.01)
*A61M 16/20* (2006.01)
(Continued)

(52) U.S. Cl.
CPC ....... *F16K 99/0048* (2013.01); *A61M 16/202* (2014.02); *A61M 16/204* (2014.02);
(Continued)

(58) Field of Classification Search
CPC ..... Y10T 137/87314; F16K 2099/0086; F16K 99/0048; F16K 99/0007; B81C 1/00182;
(Continued)

(56) References Cited

U.S. PATENT DOCUMENTS

| | | | | |
|---|---|---|---|---|
| 5,176,358 A | * | 1/1993 | Bonne | F15B 13/0405 251/30.02 |
| 5,441,597 A | * | 8/1995 | Bonne | F15B 13/0405 216/17 |

(Continued)

FOREIGN PATENT DOCUMENTS

| | | |
|---|---|---|
| CN | 103684046 A | 3/2014 |
| CN | 105805412 A | 7/2016 |

(Continued)

OTHER PUBLICATIONS

EPO Search Report and Written Opinion for co-pending EP Appl. No. 19163000.3 dated May 23, 2019 (14 pages).

(Continued)

*Primary Examiner* — Matthew W Jellett
(74) *Attorney, Agent, or Firm* — Crowe & Dunlevy

(57) ABSTRACT

A valve module includes a semiconductor body, cavities in the semiconductor body separated from each other by a distance, a cantilever structure suspended over each cavity to enable at least partial closing of the cavity, and a piezoelectric actuator for each cantilever structure. The piezoelectric actuator is configured for use to cause a positive bending of the respective cantilever structure and so modulate a rate of air flow through the valve module.

22 Claims, 11 Drawing Sheets

(51) Int. Cl.
*B81B 3/00* (2006.01)
*B81C 1/00* (2006.01)
*A61M 39/22* (2006.01)

(52) U.S. Cl.
CPC ........... *A61M 39/22* (2013.01); *B81B 3/0021* (2013.01); *B81C 1/0015* (2013.01); *B81C 1/00182* (2013.01); *F16K 99/0007* (2013.01); *A61M 2039/226* (2013.01); *A61M 2205/0294* (2013.01); *A61M 2207/10* (2013.01); *B81B 2201/054* (2013.01); *F16K 2099/0086* (2013.01); *Y10T 137/87314* (2015.04)

(58) Field of Classification Search
CPC ............ B81C 1/0015; B81B 2201/054; B81B 3/0021; A61M 2207/10; A61M 2205/0294; A61M 2039/226; A61M 39/22; A61M 16/204; A61M 16/202; A61M 16/201
See application file for complete search history.

(56) References Cited

U.S. PATENT DOCUMENTS

| | | | | |
|---|---|---|---|---|
| 5,739,832 A | * | 4/1998 | Heinzl | B41J 2/14282 347/68 |
| 5,914,507 A | | 6/1999 | Polla et al. | |
| 5,927,325 A | * | 7/1999 | Bensaoula | F16K 99/0001 137/375 |
| 6,003,833 A | * | 12/1999 | Tasi | F15C 5/00 251/11 |
| 6,270,202 B1 | | 8/2001 | Namba et al. | |
| 6,705,345 B1 | * | 3/2004 | Bifano | F15C 5/00 137/597 |
| 7,448,412 B2 | * | 11/2008 | Teach | F15C 5/00 137/596.17 |
| 2006/0049826 A1 | | 3/2006 | Daneman et al. | |
| 2014/0333703 A1 | | 11/2014 | Burkirk et al. | |
| 2017/0035985 A1 | * | 2/2017 | Newland | A61M 16/109 |

FOREIGN PATENT DOCUMENTS

| | | |
|---|---|---|
| EP | 0713773 A2 | 5/1996 |
| EP | 1275412 A2 | 1/2003 |
| EP | 3173235 A1 | 5/2017 |
| IE | 20090238 A1 | 10/2009 |
| WO | 2006097522 A1 | 9/2006 |
| WO | 2013186965 A1 | 12/2013 |
| WO | 2015167347 A1 | 11/2015 |

OTHER PUBLICATIONS

IT Search Report and Written Opinion for IT Appl. No. 102018000003552 dated Oct. 30, 2018 (13 pages).

Huff, Michael A., et al: "A Pressure-Balanced Electrostatically-Actuated Microvalve," Microsystems Technology Laboratories, Massachusetts Institute of Technology, IEEE 1990 (5 pages).

Ohnstein, T., et al: "Micromachined Silicon Microvalve," Sensor and System Development Center, Honeywell, Inc., IEEE 1990 (4 pages).

* cited by examiner

PIEZOELECTRIC VALVE MODULE, METHOD FOR MANUFACTURING THE VALVE MODULE, METHOD FOR OPERATING THE VALVE MODULE, AND RESPIRATORY AID DEVICE INCLUDING ONE OR MORE OF THE VALVE MODULES

PRIORITY CLAIM

This application claims the priority benefit of Italian Application for Patent No. 102018000003552, filed on Mar. 14, 2018, the content of which is hereby incorporated by reference in its entirety to the maximum extent allowable by law.

TECHNICAL FIELD

This disclosure relates to a piezoelectric valve module, to a method for manufacturing the valve module, to a method for operating the valve module, and to a respiratory aid device including one or more valve modules.

BACKGROUND

Known to the art are MEMS (MicroElectroMechanical System) valves, also known as microvalves, obtained with silicon-machining processes. Such valves are typically used for controlling passage of gases or fluids, and may be operated piezoelectrically or electrostatically.

MEMS valves of a known type are, however, of relatively large dimensions and are difficult to integrate in an array including hundreds of valves, while at the same time providing reduction or minimization of the size of the array as well as containment of costs. Valve arrays prove advantageous in numerous applications, in particular in conditions where fine control of the gas or fluid is desired.

In addition, valves of a known type are used in a plurality of application contexts, including the medical field, where stringent requirements of reliability and safety are present. For instance, CPAP (Continuous Positive Airway Pressure) is a method of respiratory ventilation used chiefly in the treatment of the sleep apnea, and is commonly used for patients with serious respiratory insufficiency, including new-born babies. CPAP machines are mainly used by patients in their own homes for the treatment of sleep apnea, a disorder in which the upper airways are partially restricted up to the point of occlusion during the deepest phases of sleep, causing a sharp reawakening of the subject. CPAP apparatuses manage to counter this phenomenon, supplying a flow of compressed air, through a face mask (or nasal mask) and a tube, enabling the airways to be kept open and pervious (via the pressure of the air) so that respiration remains regular. The CPAP machine delivers the air at the pressure prescribed by the medical staff.

Some patients who are candidates for use of the CPAP are reluctant to accept this therapy because the face mask (which is at times a nasal mask) and the tube that connects it to the machine prove inconvenient and cumbersome, and the flow of air that is to be administered is regulated, for some patients, at a high rate, with considerable associated noise. Some patients adapt to the treatment in a few weeks, whereas others have to carry out numerous tests (using masks and apparatuses) to be able to then adapt to everyday use. Finally, other patients interrupt or crease the treatment completely as early as during the first week of treatment.

There is a need to overcome the drawbacks of the prior art.

SUMMARY

In an embodiment, a miniaturized valve, such as a piezoelectric valve module, is provided that may be integrated in CPAP systems with less encumbrance, albeit maintaining high efficiency, compatibility with sanitary standards, possibility of adjusting the flow of air supplied, and possibility of integration in a modular system (thus providing high scalability).

In an embodiment, a method is provided for manufacturing the aforesaid miniaturized valve that will be economically advantageous and fast to implement.

In an embodiment, a mechanical ventilation device of the CPAP type includes a plurality of the aforesaid miniaturized valves.

A valve module includes an input configured to receive a first air flow and an output configured to supply a second air flow, the valve module comprising: a semiconductor body; a plurality of cavities in the semiconductor body, at a distance from one another; a plurality of cantilever structures, each of which is suspended over a respective cavity to close the respective cavity at least partially; and a plurality of piezoelectric actuators, each of which is operatively coupled to a respective cantilever structure and which are arranged so that, in use, they cause a positive bending of the respective cantilever structure so as to modulate a rate of the second air flow at output.

A respiratory aid device, for example, of a Continuous Positive Airway Pressure (CPAP) type comprises a plurality of such valve modules.

A method for manufacturing a valve module comprises: forming a plurality of cavities, at a distance from one another, in a semiconductor body; forming a plurality of cantilever structures, each of which is suspended over a respective cavity to close the respective cavity at least partially; and coupling a plurality of piezoelectric actuators to a respective cantilever structure so that the plurality of piezoelectric actuators cause, in use, a positive bending of the respective cantilever structure so as to modulate a rate of second air flow at an output.

BRIEF DESCRIPTION OF THE DRAWINGS

For a better understanding, embodiments thereof are now described, purely by way of non-limiting example, with reference to the attached drawings, wherein.

DETAILED DESCRIPTION

Figure 1:
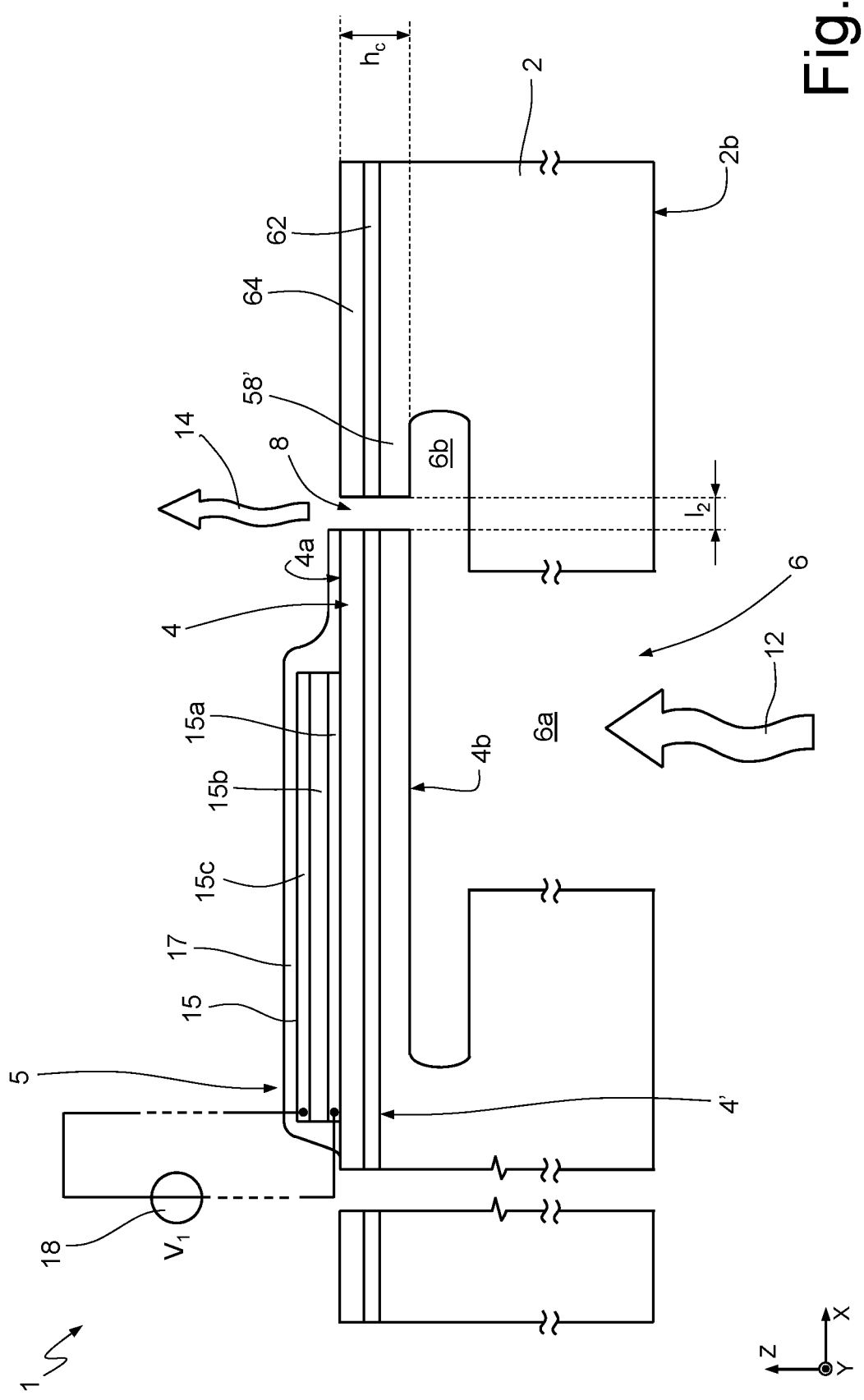
FIG. 1 is a lateral sectional view of a MEMS valve according to one embodiment of this disclosure.
Figure 2:
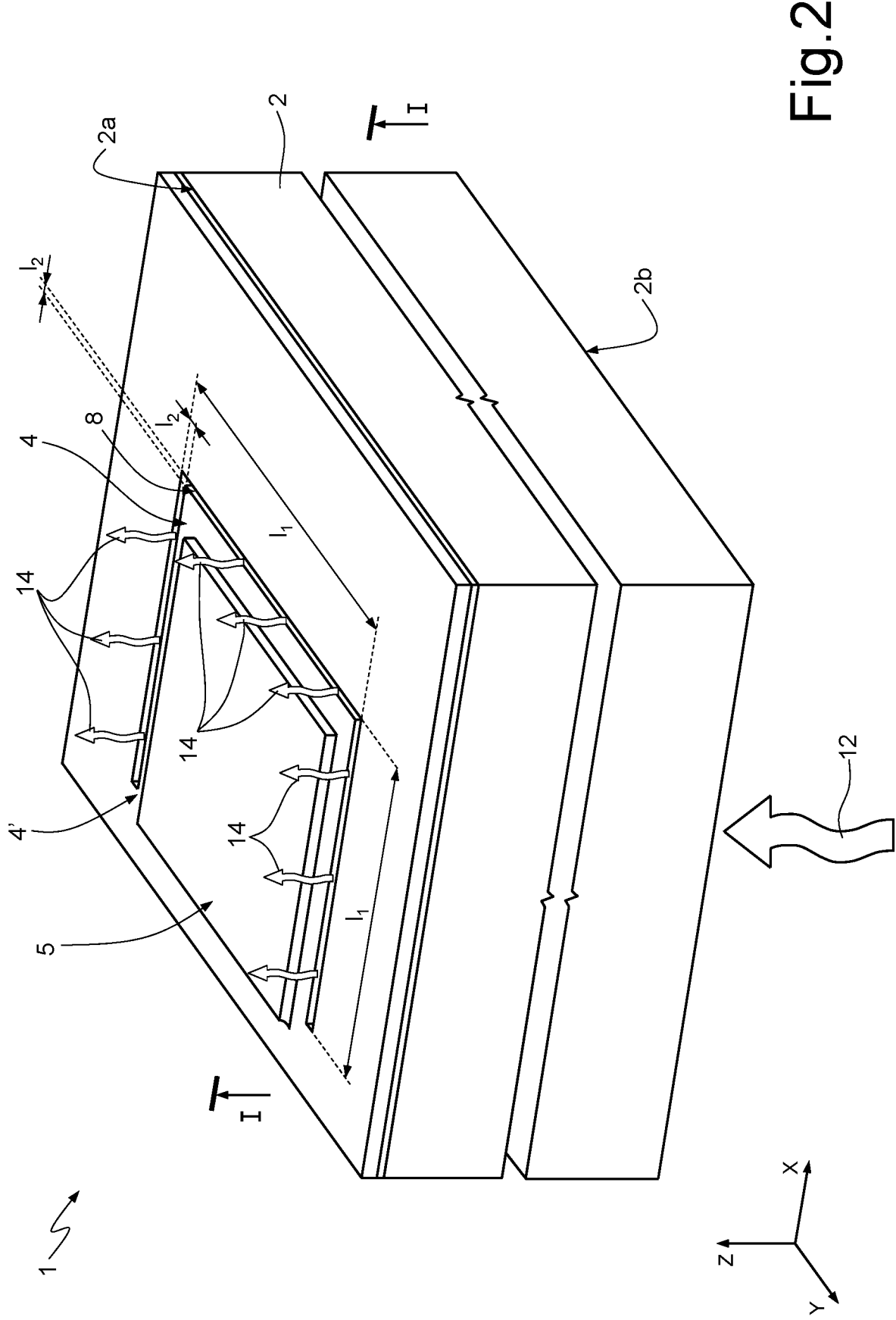
FIG. 2 is a perspective view of the MEMS valve of FIG. 1.

FIG. 1 shows, in lateral sectional view and in a reference system defined by mutually orthogonal axes X, Y, and Z, a piezoelectrically operated valve 1, according to one aspect of this disclosure. FIG. 2 illustrates a perspective view of the valve 1 of FIG. 1, in the same reference system. FIG. 1 is, in particular, a view taken along the line of section I-I of FIG. 2.

The valve 1 includes: a structural body 2, of semiconductor material such as silicon, having a front side 2a and a back side 2b opposite to one another; a cantilever structure 4, which extends on the front side 2a, having a top face 4a and a bottom face 4b; a piezoelectric actuator 5, operatively coupled to the top face 4a of the cantilever structure 4; an inlet chamber 6, which extends from the back side 2b of the structural body 2 towards the bottom face 4b of the cantilever structure 4; and a through trench 8, which partially surrounds the cantilever structure 4 and physically separates it, in part, from the structural body 2 except for at an anchoring portion 4' mechanically coupled to the structural body 2. In particular, the cantilever structure 4 has, in top plan view in the plane XY, a quadrangular shape (here, in the case in point, square) and is mechanically constrained or attached to the structural body 2 on one side thereof. The remaining three sides of the cantilever structure 4 are, as has been said, separated from the structural body 2 by the trench 8. As indicated graphically in FIG. 2, on each side of the cantilever structure 4 that the trench 8 faces, the trench 8 itself has, in the view in the plane XY, the shape of a rectangle with major side $l_1$ comprised between approximately 500 µm and 1000 µm and minor side $l_2$ comprised between approximately 0.5 µm and 10 µm.

In one embodiment, the structural body 2 and at least part of the cantilever structure 4 are formed by machining a monolithic block of semiconductor material; the anchoring portion 4' of the membrane extends seamlessly as a prolongation of the structural body 2.

In one embodiment, the cantilever structure 4 includes: a layer of silicon 58', in particular monocrystalline silicon, which extends as a prolongation of the structural body 2 and forms the anchoring portion 4'; and one or more insulating layers, of which two layers 62 and 64 are here shown, of $SiO_2$ and TEOS, respectively. For instance, the cantilever structure 4 has a thickness $h_C$ chosen as a function of the stiffness that it is desired to bestow on the cantilever structure 4 itself. For instance, the cantilever structure 4 has a thickness $h_C$ in the range 0.5 µm-50 µm.

The inlet chamber 6 includes a first portion 6a, the cross section of which has an area, in the plane XY, having a first value, and a second portion 6b, the cross section of which has an area, in the plane XY, having a second value greater than the first value. In particular, the second portion 6b forms a cavity inside the structural body 2, over which the cantilever structure 4 is directly suspended and further forms a fluidic-communication channel (in particular, here the fluid is air) between the first portion 6a of the inlet chamber and the trench 8.

The piezoelectric actuator 5 includes a band of piezoelectric material 15 that partially covers the cantilever structure 4 and, in particular, extends from the anchoring portion 4' towards the trench 8, without reaching the latter.

The band of piezoelectric material 15 comprises, in one embodiment, a stack formed by a first electrode 15a (e.g., made of Pt material), a layer of piezoelectric material 15b (e.g., made of PZT material) and a second electrode 15c (e.g., made of TiW material). Respective insulating layers extend underneath and on top of the stack 15a-15c, to insulate it electrically and protect it from external agents. The piezoelectric band 15 may thus be represented electrically as a capacitor, the first electrode 15a of which is connected to a reference voltage (e.g., ground voltage) and the second electrode 15c of which is biased by an actuation voltage.

It may further be noted that, in one embodiment, a stress-inducing layer 17, for example of silicon nitride having a thickness comprised between 0.01 µm and 1 µm, extends on the band of piezoelectric material 15, to cover the latter (completely in some applications) and to cover part of the cantilever structure 4. The material and/or thickness of the stress-inducing layer 17 are chosen so as to induce within the cantilever structure 4 a compressive stress that, in resting conditions (i.e., in conditions where the piezoelectric actuator 5 is not biased) enables the cantilever structure 4 to be kept substantially parallel to the plane XY (i.e., lying in a plane that forms a maximum angle of ±1° with respect to the plane XY).

The piezoelectric band 15 may be electrically connected to a first voltage generator 18. The voltage generator 18 is configured to bias the piezoelectric band 15 at a working voltage $V_1$ (voltage applied between the electrodes 15a and 15c) comprised between a minimum value $V_{MIN}$ (valve 1 completely closed, e.g. 0 V) and a maximum value $V_{MAX}$ (valve 1 at maximum opening allowed before structural damage ensues, e.g. 40 V). The working voltage $V_1$ may assume, during use of the valve 1, a plurality of intermediate values in the range $V_{MIN}$-$V_{MAX}$, as a function of the (more or less accentuated) bending that it is desired to obtain for the cantilever structure 4.

Figure 3:
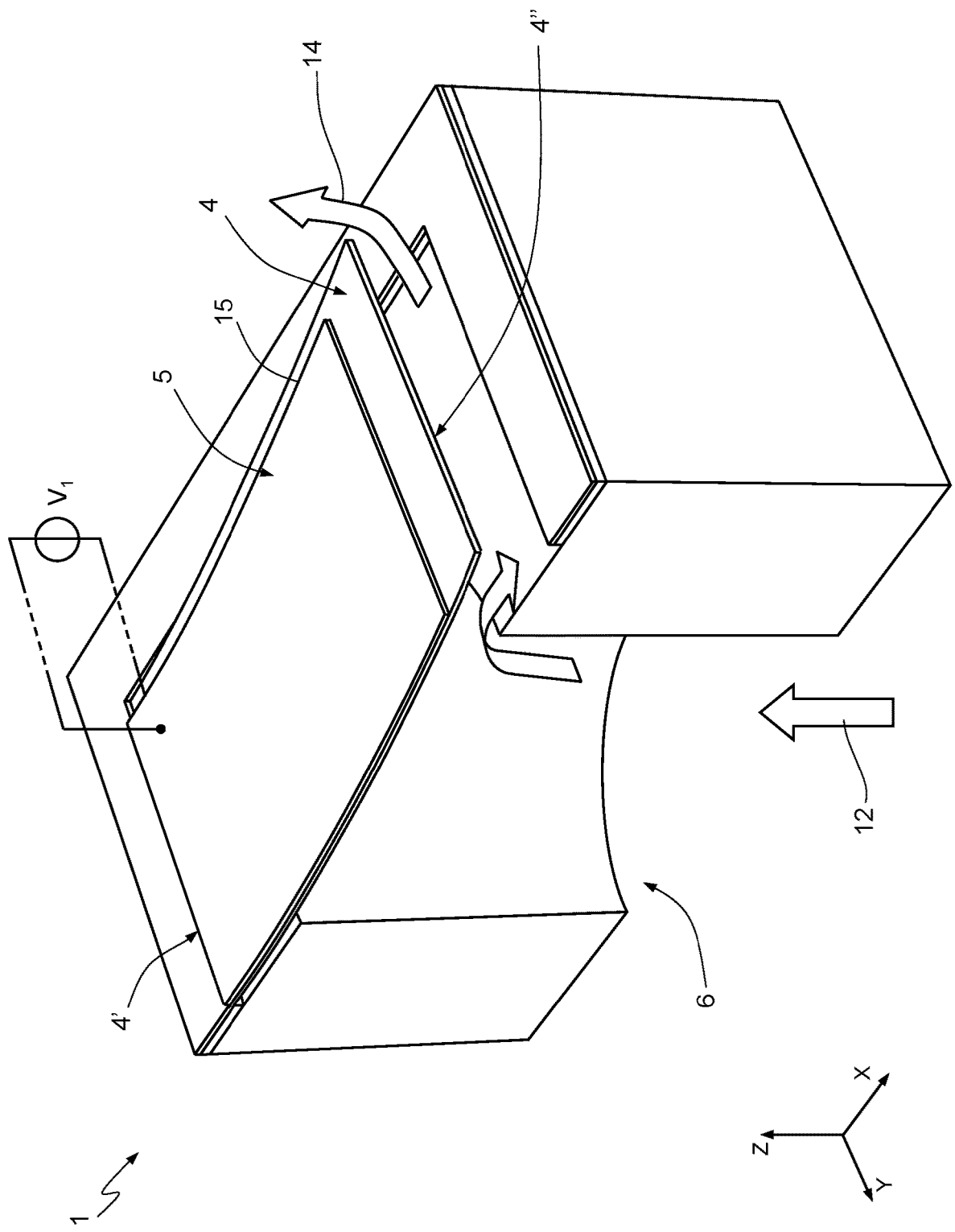
FIG. 3 is a perspective view of the MEMS valve of FIG. 2, sectioned and in an operating condition where the valve is open or partially open.

FIG. 3 shows, in perspective view, a portion of the valve 1 during an operating condition where the valve is at least partially open. In particular, the portion illustrated in FIG. 3 is sectioned along the line of section I-I of FIG. 2. As may be noted, when the band of piezoelectric material 15 is biased at the working voltage $V_1$, it induces a stress in the cantilever structure 4, which consequently bends. In other words, the stress induced in the PZT by the electrical field generated by the working voltage $V_1$, generates in the cantilever structure 4 a tensile stress, which causes downward bending, also known as "positive bending", of the cantilever structure 4. As a consequence of the fact that the cantilever structure 4 is constrained or attached to the structural body at or only at the anchoring portion 4', positive bending entails a translation upwards of the opposite free end (designated by the reference number 4").

In an operating condition of the valve 1 where the inlet chamber 6 receives a flow of air (represented by the arrow 12) directed towards the cantilever structure 4, the flow of air, passing through the first and second portions 6a, 6b of the inlet chamber 6, flows out through the trench 8 (as represented by the arrow 14).

The stiffness of the cantilever structure 4 is chosen as a function of the pressure exerted, in use and in the positive direction of the axis Z, by the flow of air 12 on the cantilever structure 4. In particular, the stiffness of the cantilever structure 4 is chosen so that, in the condition where the valve 1 is off (i.e., with the piezoelectric actuator 5 not biased), the maximum possible flow of air 12 (which depends upon the specific application and upon the use of the valve 1) will not cause bending of the cantilever structure 4 such as to open the valve 1 even partially. Possible tolerances for partial opening of the valve 1 in the off state, caused by the flow of air 12, may be envisaged, once again on the basis of the specific application.

By way of non-limiting example, a cantilever structure 4 of the type described previously, of a thickness $h_C=15$ μm, may withstand a pressure of the flow of air 12 of 2000 Pa, without presenting significant displacement (i.e., accepting a tolerance of ±0.1°) from its position of lie in the plane XY.

As a consequence of what has been described above, in the operating condition illustrated in FIG. 3, the flowrate, or volume, of air 14 at output increases when the cantilever structure 4 is positively bent (as illustrated in FIG. 3) with respect to the operating condition illustrated in FIG. 2. Intermediate positions are possible by modulating the value of the applied voltage $V_1$ between the minimum value $V_{MIN}$ and the maximum value $V_{MAX}$. It is thus possible to modulate the flow of air 14 (or, in other words, the flowrate) at outlet from the valve 1.

It should be noted that, according to one aspect of this disclosure, on account of the presence of the trench 8, the valve 1 is not fluid-tight. This means that a flow of air 14 at the outlet, albeit low or even minimal, is present also with the valve off, or closed, but in the presence of the flow of air 6 at the inlet. By reducing or minimizing the size of the trench 8 it is possible to reduce or minimize accordingly the flowrate, or volume, of air supplied at outlet in conditions of valve closed.

Figure 4:
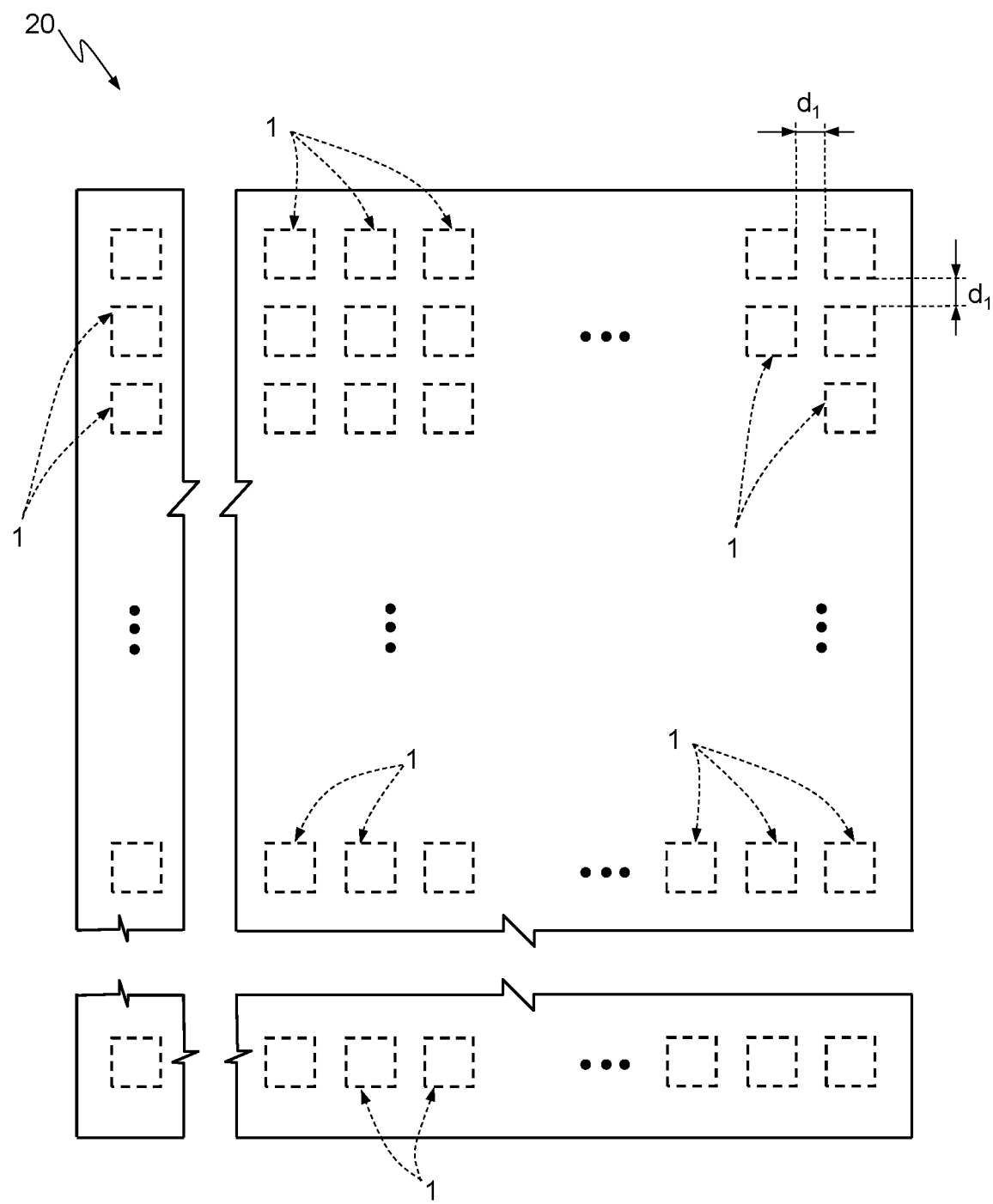
FIG. 4 is a top plan view of a valve module that includes a plurality of MEMS valves of the type illustrated in FIGS. 1-3.

FIG. 4 shows, in top plan view (in the plane XY), a valve module 20 comprising a semiconductor die integrating a plurality of valves 1, arranged alongside one another to form an array of valves 1. The semiconductor die 20 has, by way of example, a square shape, for instance with a side comprised between 10 mm and 20 mm, and houses a plurality (e.g., between 200 and 500, more in particular between 300 and 350) of valves 1 having, by way of example, a square shape, with a side comprised between 600 μm and 900 μm, separated from one another by a distance $d_1$ comprised between 15 μm and 30 μm.

For instance, consider the following design parameters: constant pressure of 2000 Pa of the flow of air 12 at inlet to each valve 1; flowrate of the valve module 20 in the closed state (piezoelectric actuators 5 biased at $V_{MIN}=0$ V) of 0.5 l/min; and flowrate of the valve module 20 in the open state (piezoelectric actuators 5 biased at $V_{MAX}=40$ V) of 20 l/min. It is possible to design the valve module 20 having a square shape with a side of 15 mm, housing 324 cantilever structures 4, which each have a square shape with a side of 800 μm, and to size the stiffness of each cantilever structure 4 and each trench 8 so that the leakage of each valve 1 in the off, or closed, state is 0.0015 l/min and the flowrate of each valve 1 in the open state is 0.06 l/min. Design of the stiffness of each valve 1 and of the size of the trench 8 may be made by FEM (Finite-Element Method) modeling software, exploiting appropriate computer program products available to the person skilled in the art.

Figure 5:
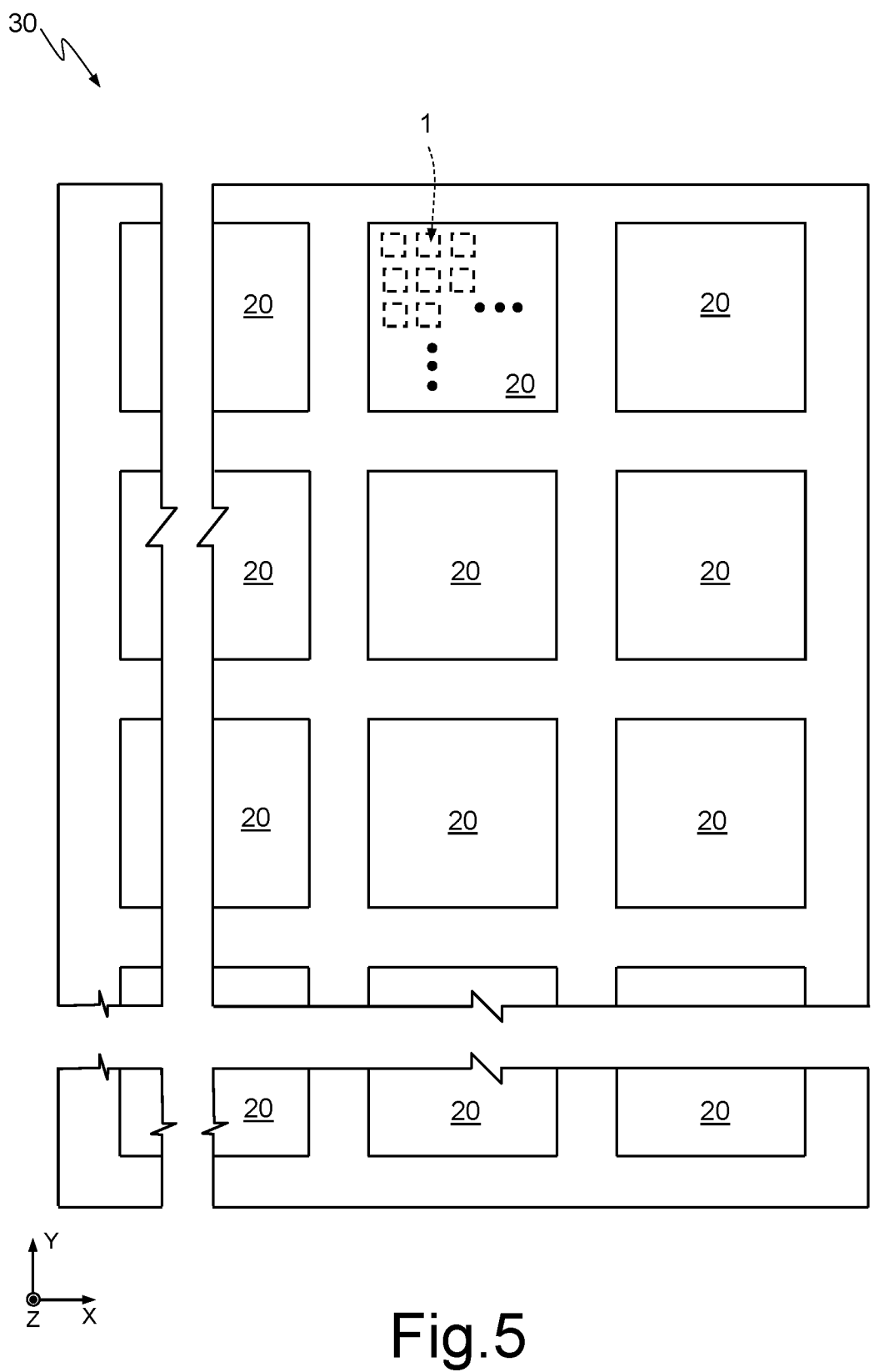
FIG. 5 is a top plan view of an array of valve modules of the type illustrated in FIG. 4.

FIG. 5 shows, in top plan view (in the plane XY), a system 30 including a plurality of valve modules 20 of the type illustrated in FIG. 4, arranged alongside one another to form an array of valve modules 20.

For instance, consider the same design parameters mentioned above: constant pressure of 2000 Pa of the flow of air 12 at inlet to each valve 1; flowrate of the valve module 20 in the closed state (piezoelectric actuators 5 biased at $V_{MIN}=0$ V) of 0.5 l/min; and flowrate of the valve module 20 in the open state (piezoelectric actuators 5 biased at $V_{MAX}=40$ V) of 20 l/min. It is possible to design the system 30 by arranging alongside one another four valve modules 20, each of which has a square shape with a side of 7.5 mm and houses 81 cantilever structures 4, each having a square shape with a side of 800 μm, and to size the stiffness of each cantilever structure 4 and each trench 8 so that the leakage of each valve 1 in the off, or closed, state will be 0.0015 l/min and the flowrate of each valve 1 in the open state will be 0.06 l/min. Design of the stiffness of each valve 1 and of the size of the trench 8 may be carried out by FEM (Finite-Element Method) modeling software, exploiting appropriate computer program products available to the person skilled in the art.

Alternatively, according to a further embodiment provided by way of example, it is possible to design the system 30 by arranging nine valve modules 20 alongside one another, each of which has a square shape with a side of 5 mm and houses 36 cantilever structures 4, each having a square shape with a side of 800 μm, and to size the stiffness of each cantilever structure 4 and each trench 8 so that the leakage of each valve 1 in the off, or closed, state is 0.0015 l/min and the flowrate of each valve 1 in the open state is 0.06 l/min.

With joint reference to FIGS. 4 and 5, it may be noted that electrical contacts (not illustrated in detail) may be integrated in the module 20 of FIG. 4 or in the modules 20 of the system 30 of FIG. 5 for biasing, in use, each valve 1. It is possible to provide dedicated electrical connections for each valve 1 so that each valve 1 may be controlled individually and independently of the other valves 1. Alternatively, it is possible to provide electrical connections common to a set of valves 1 so that the valves 1 belonging to this set may be operated jointly and independently of the valves 1 belonging to other sets. A set of valves 1 may include all the valves 1 belonging to a module 20, or else only some valves 1 belonging to a module 20.

Again, it is possible to provide electrical connections common to all the valves 1 so that all the valves 1 may be operated jointly.

For reasons of layout and optimization of routing of the electrical connections, it is likewise possible to provide a plurality of dedicated electrical connections for each valve 1 or for sets of valves 1 and operate some or all of the valves 1 jointly, coupling them together to respective one or more shared voltage generators.

With reference to FIGS. 6-15, a method for manufacturing the valve 1 of FIGS. 1-3 is now described. It is evident that the method described here may be applied to joint manufacture of a plurality of valves on a same semiconductor wafer, to form one or more modules 20 of the type illustrated in FIG. 4.

Figure 6:
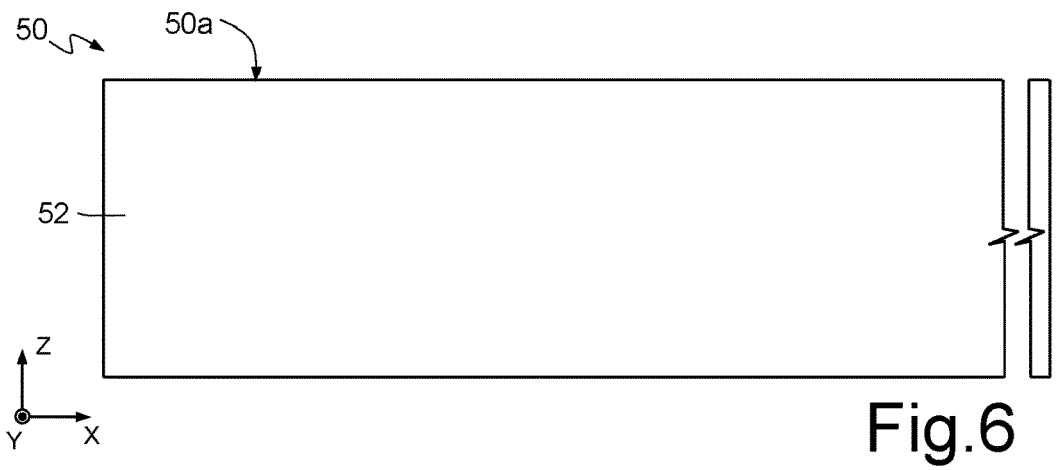
FIGS. 6-15 illustrate, in lateral sectional view, steps for manufacturing at least one MEMS valve of the type illustrated in FIGS. 1-3.

With reference to FIG. 6, a semiconductor wafer 50 is provided, in particular including a substrate 52 of monocrystalline silicon. In particular, the wafer 50 may be of a pre-machined type, and may include further layers of semiconductor, dielectric, insulating materials, or other materials (not illustrated herein). The wafer is delimited by a front side 50*a* and by a back side 50*b*, opposite to one another along the axis Z, and has a thickness, along Z, for example comprised between 300 and 800 μm.

Figure 7A:
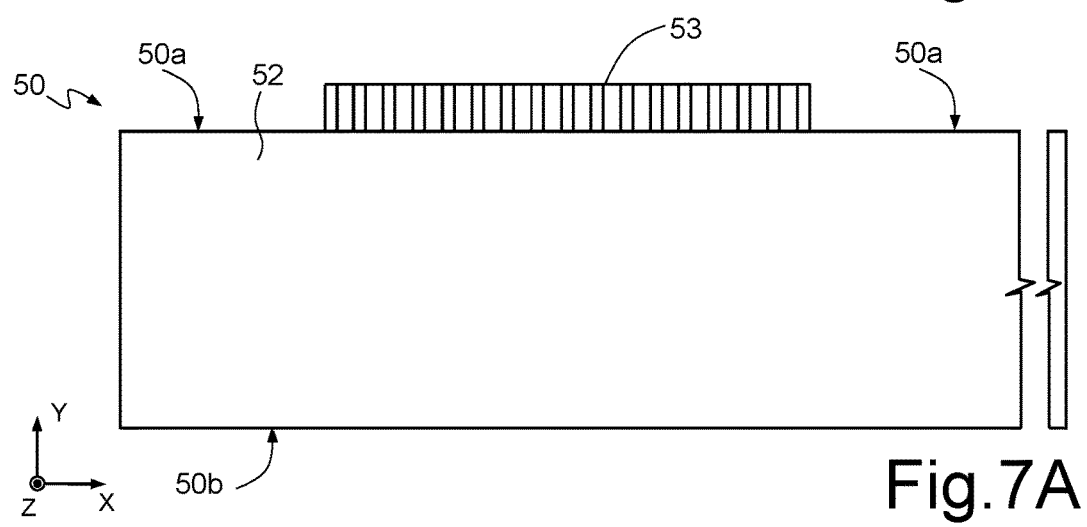
Figure 7B:
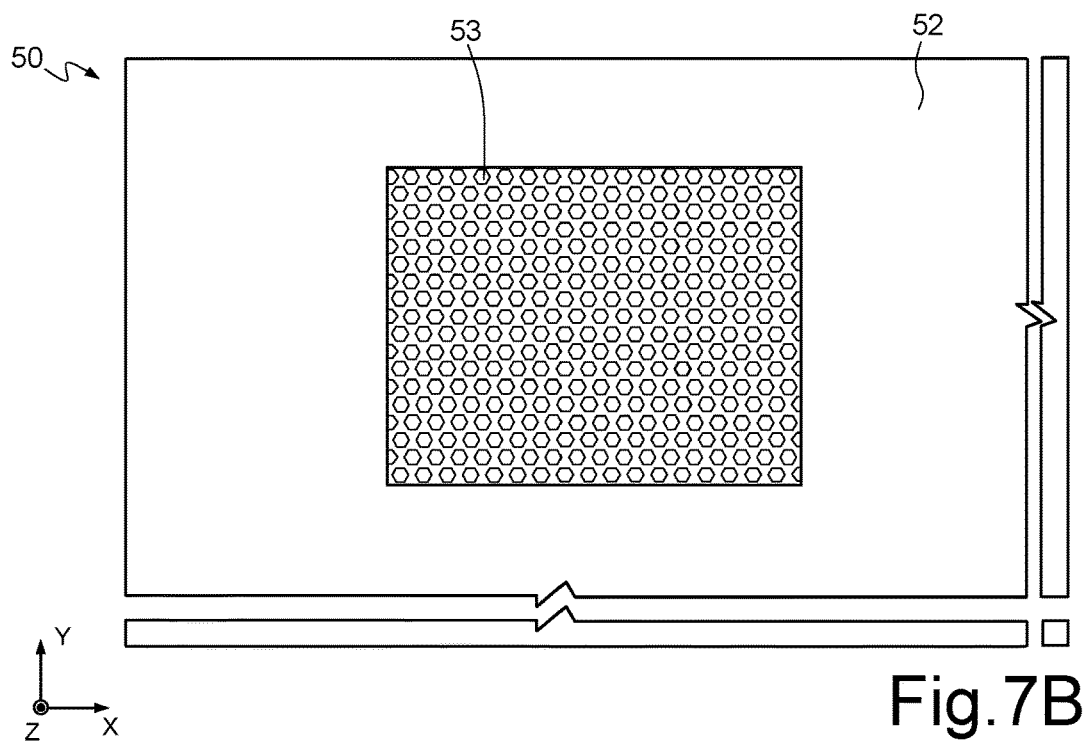
Figure 8:
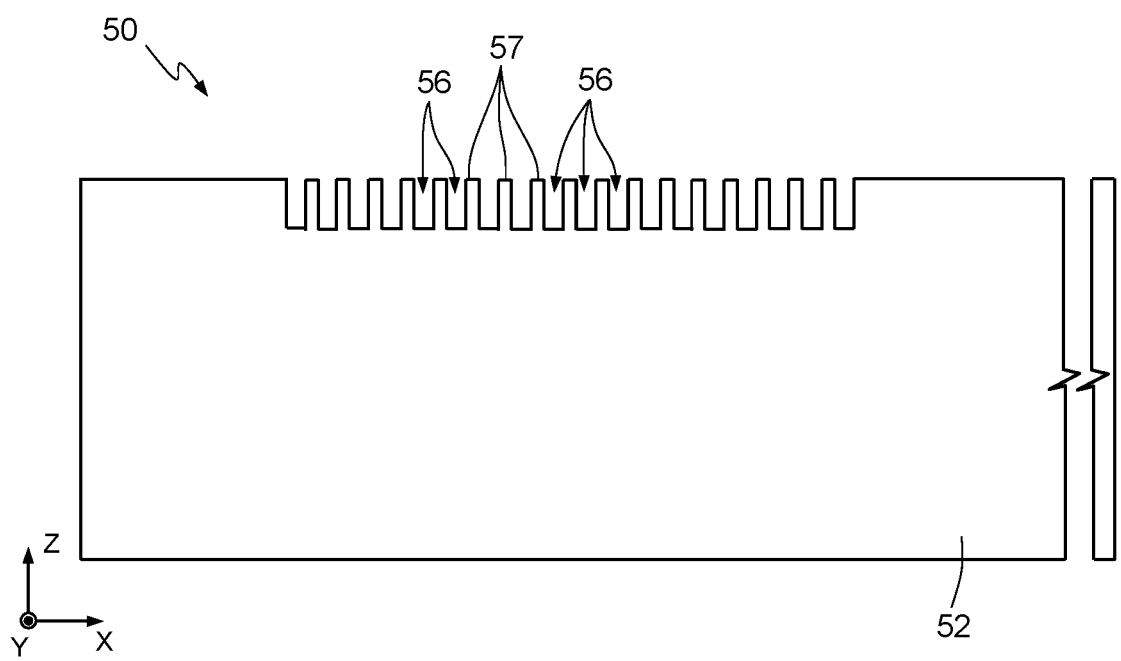
Figure 9:
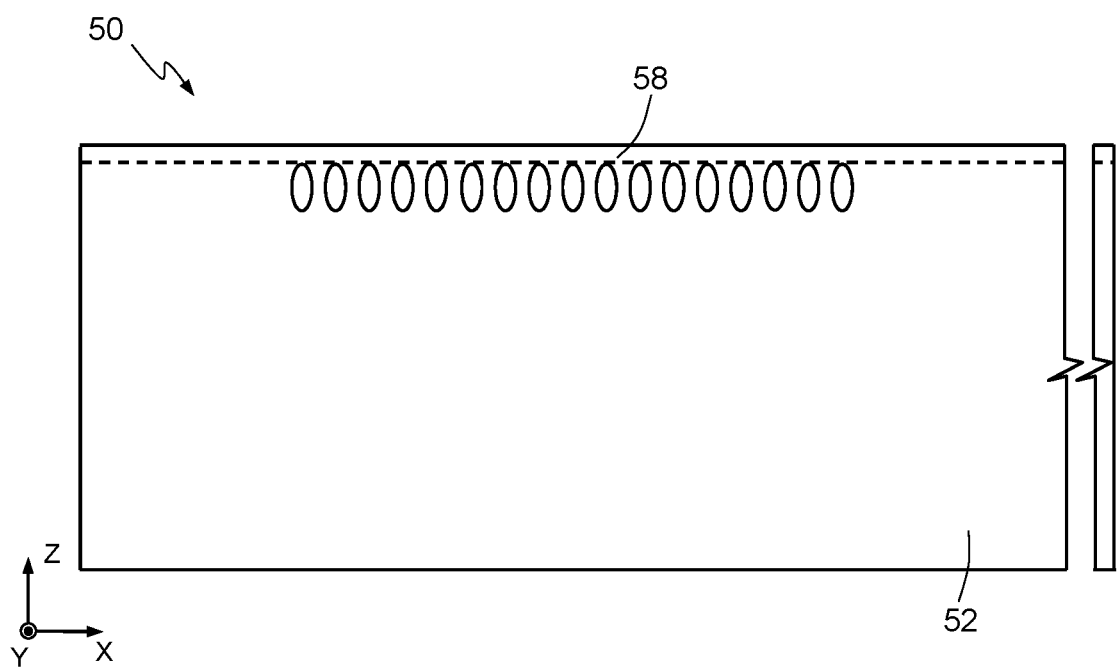
Figure 10:
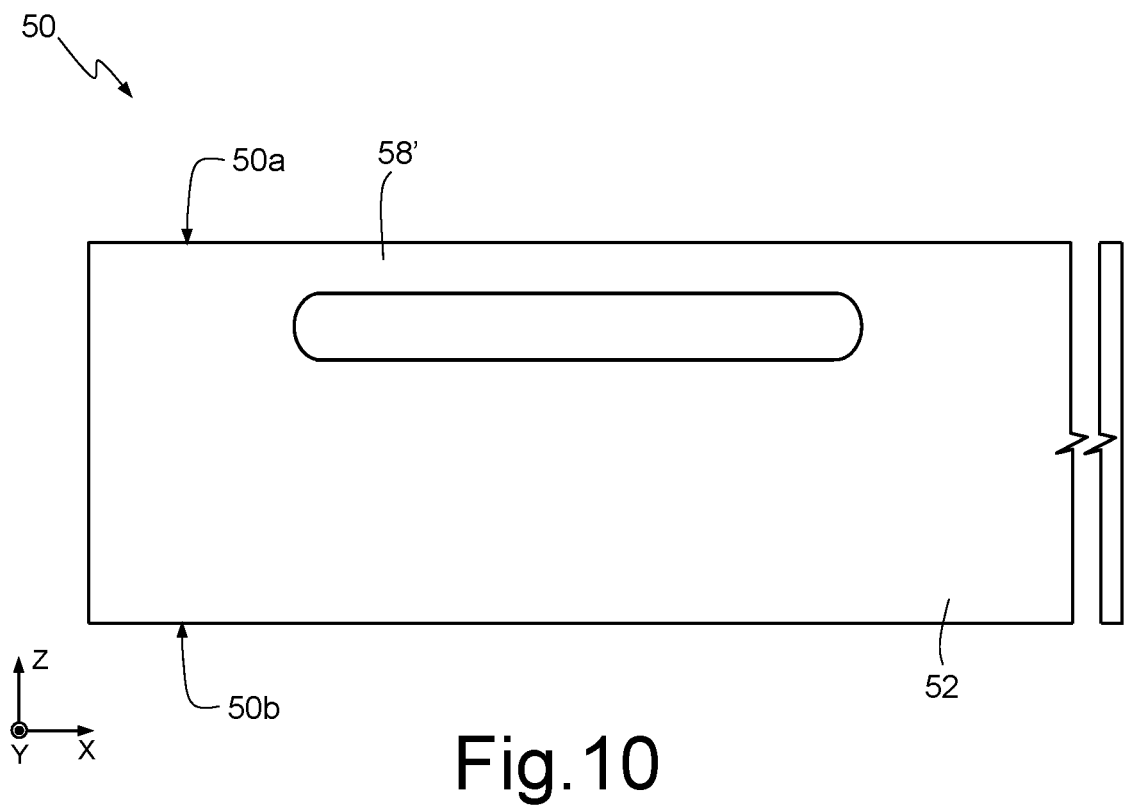
Figure 11:
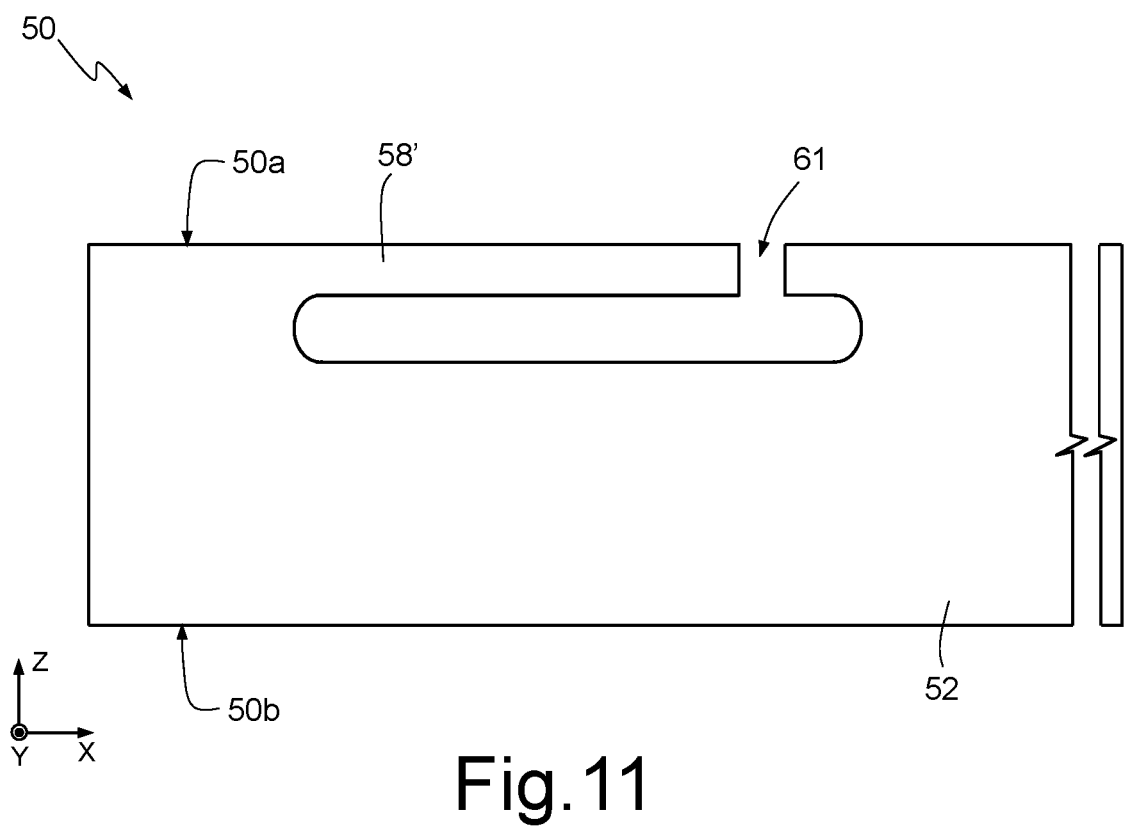
Figure 12:
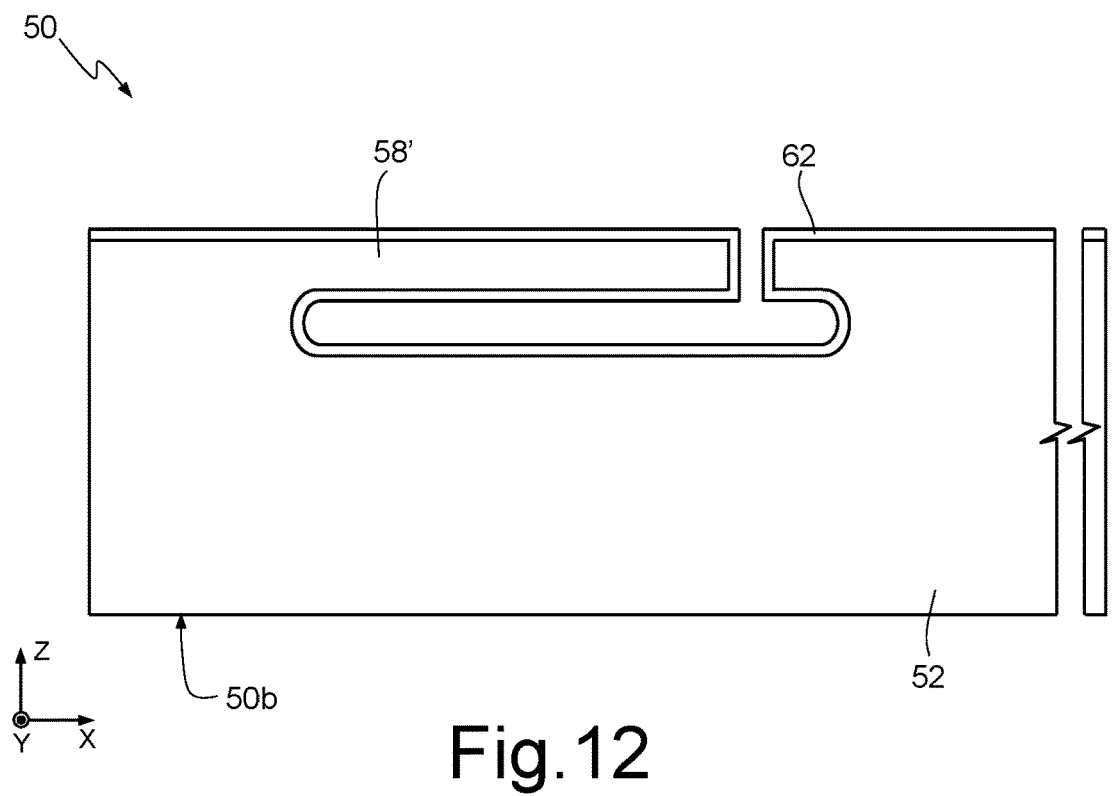

With joint reference to FIG. 7A (in lateral sectional view) and to FIG. 7B (in top plan view), by a photolithographic step, a photoresist mask 53 is provided on the semiconductor body 52 (on the front side 50*a*). The mask 53 is formed in regions of the semiconductor body 52 where the second portion 6*b* of the inlet chamber 6 is to be formed and likewise defines the shape of the cantilever structure 4 (i.e., it defines the suspended portion that is free to bend in use).

The mask 53 is shaped like a honeycomb lattice, and has mask regions, for example hexagonal, arranged close to one another.

Using the mask 53 (FIG. 8), etching of the semiconductor body 52 is carried out to form trenches 56 having a depth of some microns, for example between 5 µm and 25 µm. The trenches 56 define silicon columns 57 that are substantially the same as one another and have a shape corresponding to the shape of the honeycomb regions defined by the mask 53. By way of example, each column 57 has a diameter of approximately 1 µm and is separated from an adjacent column, along X or along Y, by approximately 1 µm. In general, the diameter and spacing of the columns 57 are chosen with a value such as to enable closing of the trenches 56 at the top during the step of epitaxial growth described hereinafter.

Next (FIG. 9), the mask 53 is removed and an epitaxial growth is carried out in a deoxidizing environment (typically, in atmosphere presenting high concentration of hydrogen, preferably using trichlorosilane—$SiHCl_3$). The epitaxial growth is carried out at least until the trenches 56 are closed at the top (for example, for 45 s at a temperature close to 1200° C.).

Consequently, an epitaxial layer 58 grows on top of the silicon columns 57, closes the trenches 56 at the top, and traps therein the gas present (here, hydrogen molecules—$H_2$).

An annealing step is then carried out, for example for approximately 30-40 min at a temperature of approximately 1190-1200° C. The annealing step causes (FIG. 10) a migration of the silicon atoms, which tend to move into the position of lower energy, in a per se known manner, as, for example, discussed in the paper by T. Sato, N. Aoki, I. Mizushima, and Y. Tsunashima, "A New Substrate Engineering for the Formation of Empty Space in Silicon (ESS) Induced by Silicon Surface Migration", IEDM 1999, pp. 517-520 (incorporated by reference).

At the trenches 56, where the silicon columns are close together, the silicon atoms migrate completely and form a buried cavity, closed at the top by a suspended layer 58' (membrane).

Preferably, annealing is carried out in $H_2$ atmosphere so as to prevent the hydrogen present in the trenches 56 from escaping through the epitaxial layer outwards and so as to increase the concentration of hydrogen present in the buried cavity in the case where the hydrogen trapped during the step of epitaxial growth were not sufficient. Alternatively, annealing may be carried out in a nitrogen environment.

The thickness, along Z, of the suspended layer 58' concurs in defining the final thickness of the cantilever structure 4. Thus, the step of growth of the epitaxial layer 58 is carried out so as to enable growth of a layer of a desired thickness (in particular, by monitoring times and conditions of growth). It is in any case possible to carry out a step of grinding, or of non-masked etching, of the front side 50 of the wafer 50, to thin out, if necessary or desired, the thickness of the epitaxial layer 58 (in particular, of the suspended layer 58').

In one embodiment, the suspended layer 58' has a final thickness of approximately between 5 µm and 25 µm.

Then (FIG. 11), masked etching is carried out (by lithographic and etching steps in themselves known) on the front side 50a of the wafer 50, to form a through hole 61. Etching is carried out so as to remove selective portions of the suspended layer 58', throughout the thickness of the suspended layer 58', until the underlying buried cavity is reached. The buried cavity is thus arranged in fluid communication with the external environment.

Next (FIG. 12), a step of oxidation of the wafer 50, for example thermal oxidation, is carried out to form an oxide layer 62. Alternatively, the oxide layer 62 may be deposited. In particular, the oxide layer 62 is formed on the front side 50a of the wafer 50 (i.e., on the suspended layer 58') and on the internal walls of the buried cavity, through the through hole 61. The thickness of the oxide layer 62 is of a few microns, for example between 1 and 2 µm. The oxide layer 62 has, in particular, the function of etch-stop layer during silicon etching to form the first portion 6a, as for example illustrated in FIG. 15. Without this layer, etching would proceed towards the silicon that forms the suspended membrane. The oxide layer 62 may likewise have a protective function, or a function of compatibility, according to the operating environment of the valve 1.

It is evident that other materials, different from silicon oxide, may be used with the same function.

A subsequent step (FIG. 12), envisages formation, on the front side 50a of the wafer 50, on the oxide layer 62, of a TEOS layer 64. The TEOS layer 64 has the function of obstructing the hole created previously for oxidizing the inside of the second portion 6b of the chamber 6, in addition to planarizing the front side of the wafer being processed. To achieve these aims, the TEOS layer 64 is chosen of an adequate thickness, for example of approximately 1 µm. It is evident that other materials, different from TEOS, may be used with the same function.

Next, steps of formation of the piezoelectric actuator 5 on the TEOS layer 64 are carried out. The piezoelectric actuator 5 is formed at least in part on the suspended layer 58', according to the layout described previously with reference to FIGS. 1 and 2.

Figure 13:
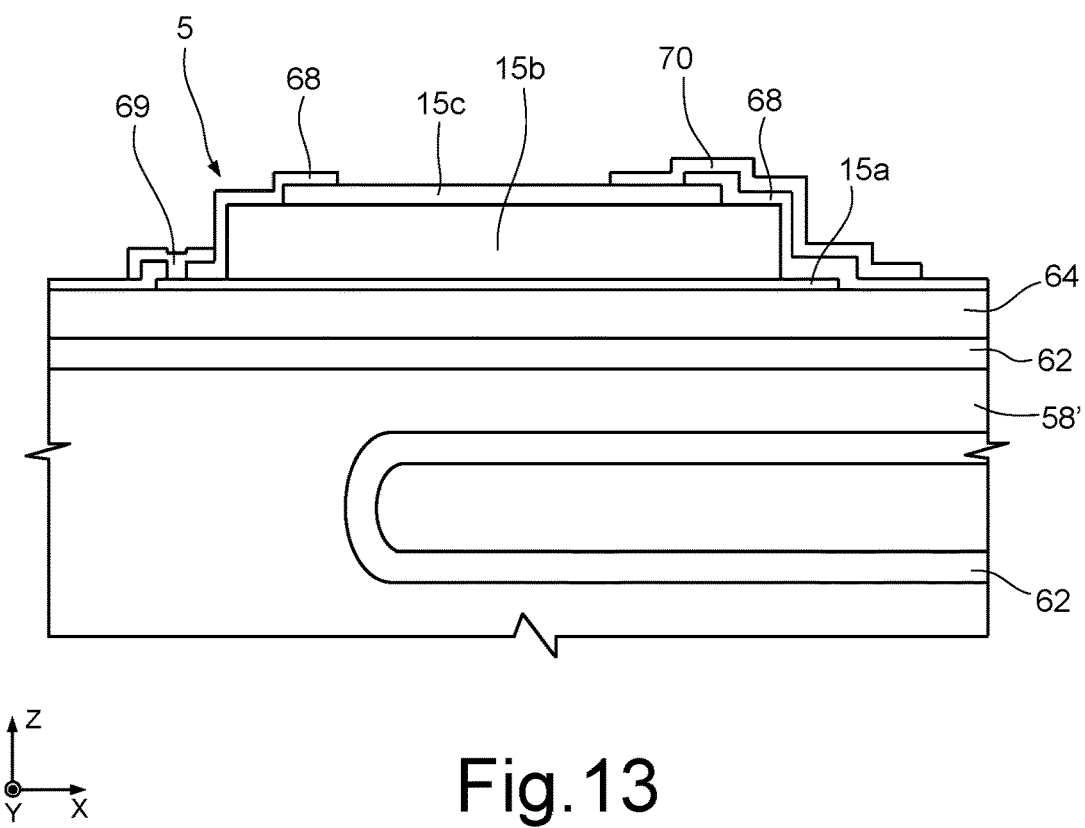
Figure 14:
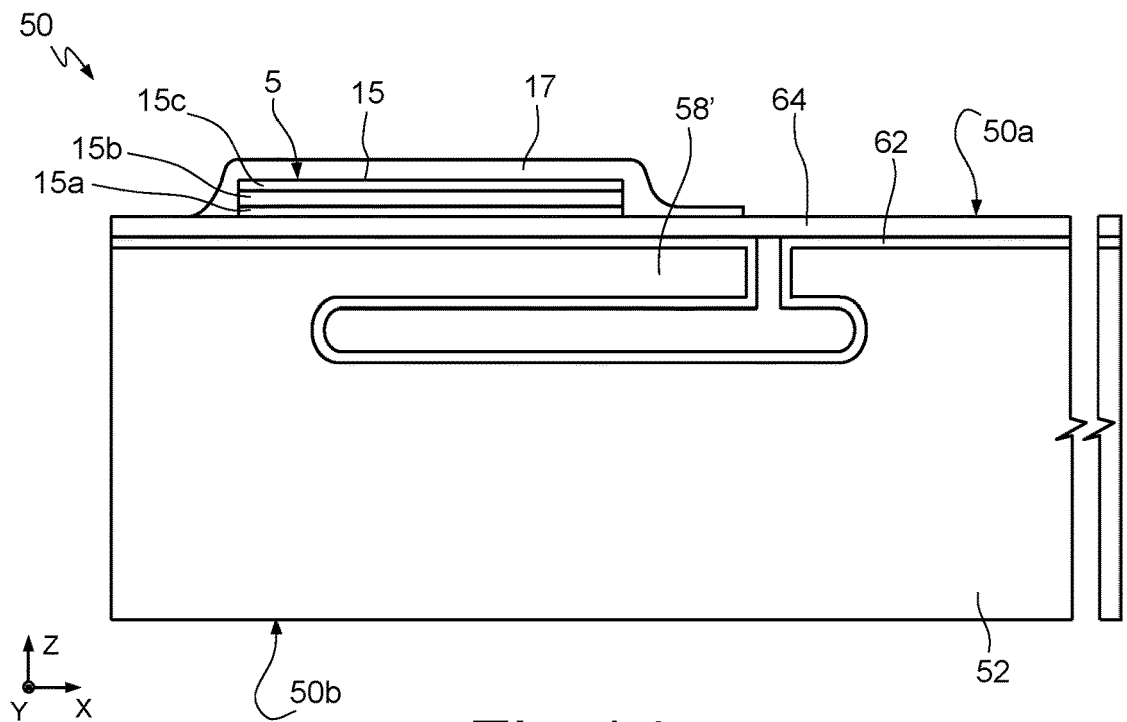
Figure 15:
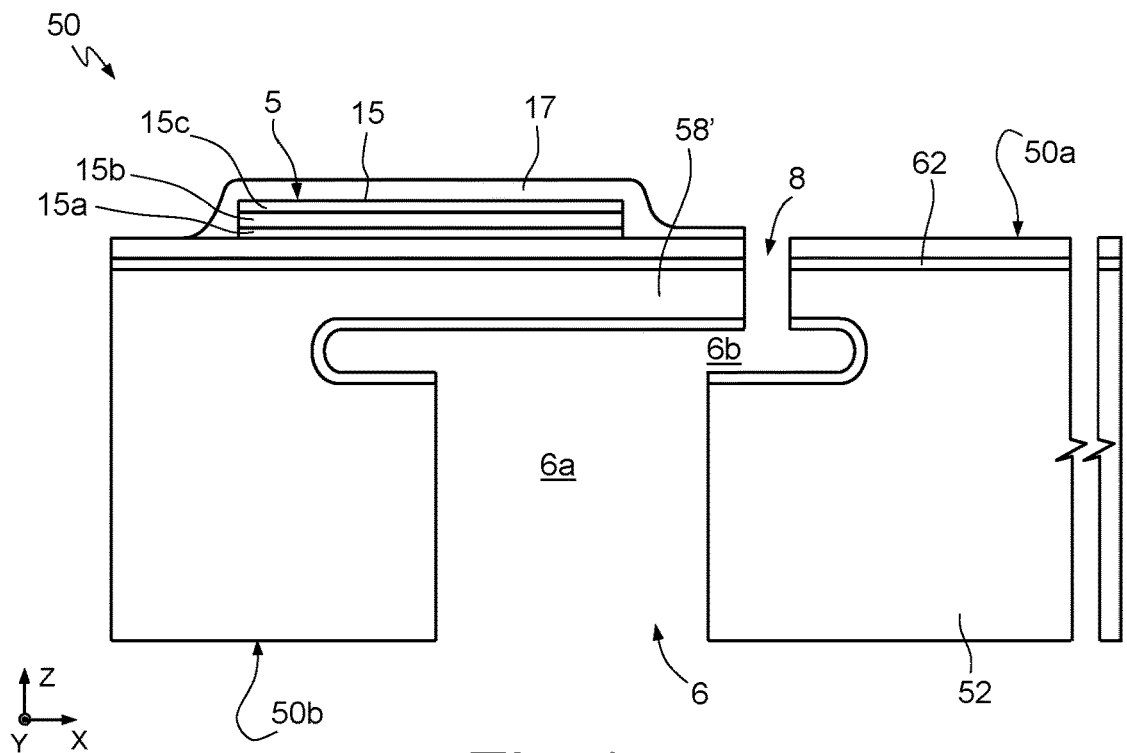

With reference to FIG. 13, which shows an enlarged view of a portion of the wafer 50 of FIGS. 6-12, steps for manufacturing the piezoelectric actuator 5 are now described. In brief, formed on the TEOS layer 64 is the bottom electrode 15a (for example, of titanium dioxide, $TiO_2$, with a thickness of, for example, between 5 and 50 nm, deposited on which is a layer of platinum, Pt, with a thickness of, for example, between 30 and 300 nm). Next, deposition of the piezoelectric layer 15b is carried out on the bottom electrode 15a, by depositing a layer of lead-zirconium-titanium trioxide (Pb—Zr—$TiO_3$, i.e., PZT) having a thickness, for example, comprised between 0.5 and 3.0 µm. Then, deposited on the piezoelectric layer 15b is a second layer of conductive material, e.g., platinum (Pt) or iridium (Ir) or iridium dioxide ($IrO_2$) or titanium-tungsten (TiW) or ruthenium (Ru), having a thickness, for example, comprised between 30 and 300 nm, to form the top electrode 15c.

The electrode layers 15a, 15c and the piezoelectric layer 15b are subjected to lithographic and etching steps, to pattern them in a desired way, thus completing formation of the piezoelectric actuator 5.

One or more passivation layers 68 are then deposited on the top electrode 15c. The passivation layers include dielectric materials used for electrical insulation of the electrodes, for example, layers of silicon oxide ($SiO_2$) or silicon nitride (SiN) or aluminum oxide ($Al_2O_3$), whether single or stacked on top of one another, of a thickness, for example, comprised between 10 nm and 1000 nm. The passivation layers are then etched in selective regions to create trenches for access to the bottom electrode 15a and the top electrode 15c. Then, a step is carried out of deposition of conductive material, such as metal (e.g., aluminum, Al, or else gold, Au, possibly together with barrier and adhesion layers, such as titanium, Ti, titanium-tungsten, TiW, titanium nitride, TiN, tantalum, Ta, or tantalum nitride, TaN), within the trenches thus created and on the passivation layers 68. A subsequent patterning step enables formation of conductive paths 69, 70 that enable selective access to the top electrode 15c and the bottom electrode 15a, for electrical biasing thereof during use. It is further possible to form further passivation layers (e.g., of silicon oxide, $SiO_2$, or silicon nitride, SiN) to protect the conductive paths 69, 70. Formation of the piezoelectric actuator 5 is thus completed.

Next (FIG. 14, which reproduces the same cross-sectional view of the wafer 50 as that of FIGS. 6-12), the stress-inducing layer 17 (previously mentioned with reference to FIG. 1) is formed on the piezoelectric actuator 5.

Then (FIG. 15), the TEOS layer 64, the oxide layer 62, and the suspended layer 58' are selectively etched (throughout their thickness) in regions thereof that extend alongside, and at a distance from, the piezoelectric actuator 5, until the underlying buried cavity is reached and the through trench 8 is thus formed. In this way, the buried cavity (which, at the end of the manufacturing steps, will become the second portion 6b of the inlet chamber 6) is in fluid connection with the external environment.

Finally, the wafer 50 (in particular, the semiconductor body 52 and the oxide layer 62 inside the buried cavity) is etched on the back side 50b so as to form the first portion 6a of the inlet chamber 6 on the side opposite to the side that houses the piezoelectric actuator 5. Etching proceeds until the buried cavity is reached (second portion 6b of the inlet chamber 6). The process of formation of the inlet chamber 6 is thus concluded.

A subsequent sawing (or dicing) step (not illustrated) enables separation from one another of dice including a valve 1 or a plurality of valves 1, thus forming a plurality of valve modules 20 of the type described previously.

Figure 16:
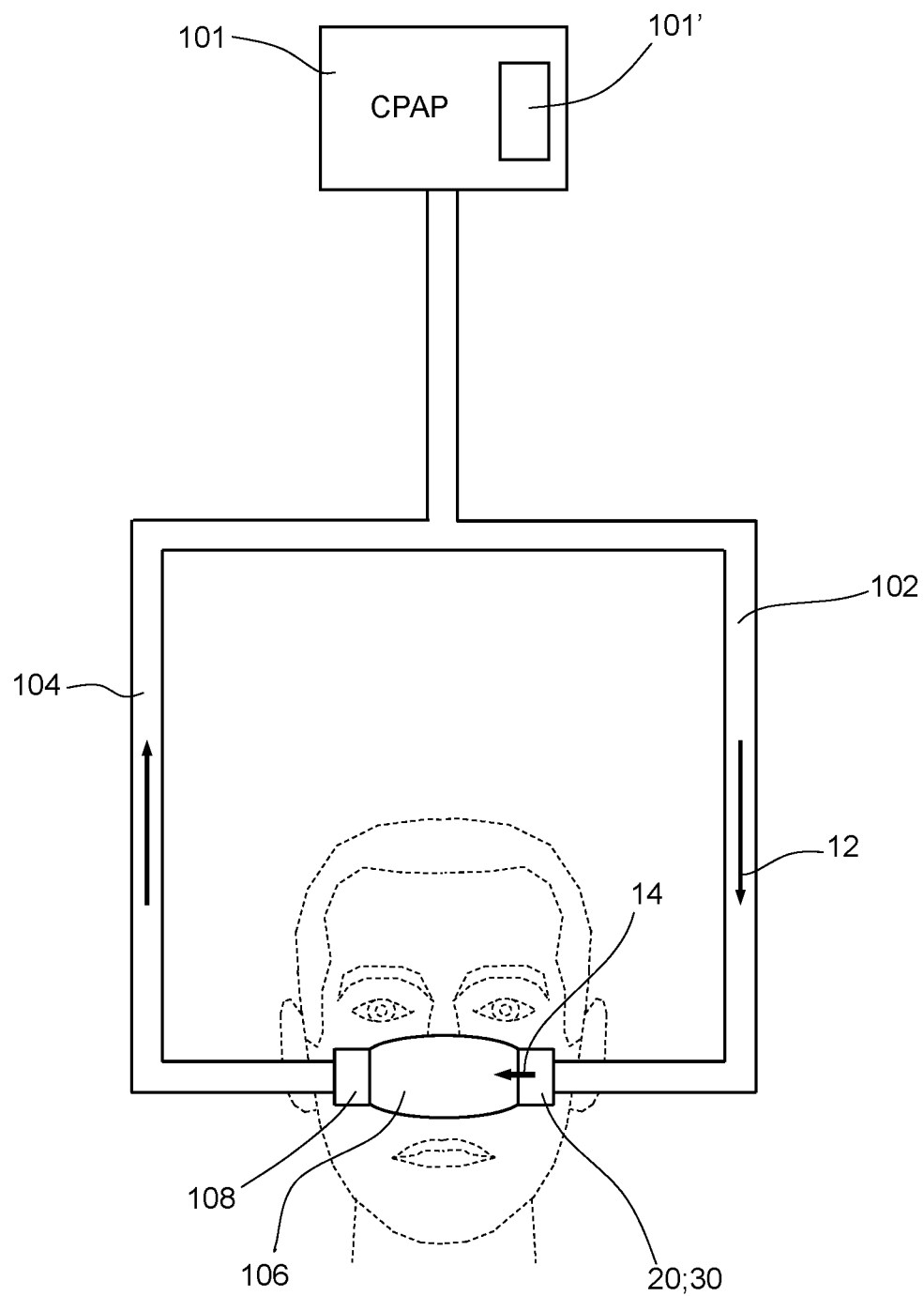
FIG. 16 is a schematic illustration of a device that houses a valve module of the type illustrated in FIG. 4 or an array of valve modules of the type illustrated in FIG. 5.

According to one aspect of this disclosure, a respiratory aid device 100, illustrated schematically in FIG. 16, is likewise provided. The respiratory aid device 100, according to an aspect of this disclosure, includes at least one valve module 20 or a system 30 formed by an array of valve modules 20 designed to supply a flow of air that is modulated or may be modulated for a user of the respiratory aid device 100 itself.

In a possible embodiment, the respiratory aid device 100 includes: a CPAP unit 101, including an air generator 101', configured to generate a mechanical ventilation of a CPAP type (flow of air 12 in FIG. 1); an inhalation channel 102, having a first end 102' coupled to the air generator 101 to receive the flow of air 12; a first valve module 20 (or a first valve system 30), according to the present disclosure, operatively coupled to a second end 102" of the inhalation channel 102 for receiving at the cavity/cavities 6 the flow of air 12; a respiration module 106, configured to be worn by a user by applying it to the nostrils and/or the mouth, coupled to the valve module 20 (or a valve system 30) in a position corresponding to the trenches 8, so as to supply the flow of air 14 at outlet to the nostrils and/or the mouth of the user; second valves 108 (of the type according to the present disclosure or of a known type), operatively coupled to the respiration module 106 for receiving a flow of air breathed out by the user; and a return channel 110, operatively coupled to the second valves 108 for receiving the flow of air breathed out and conveying it towards the CPAP unit.

It may be noted that the elements that form the device 100 may be integrated in a case of small size (for example, a few centimeters of length/width/thickness) so that it is far from cumbersome, practical to use, and portable.

From an examination of the characteristics described and illustrated herein, the advantages afforded are evident.

In particular, the valve according to this disclosure is based upon a monolithic structure (load-bearing body and cantilever structure), providing high strength and absence of components that might detach and, when used in CPAP devices, be inhaled inadvertently by the user.

Further, the piezoelectric actuation is highly controllable with low currents, thus reducing the electromagnetic field generated by the device during use.

Furthermore, the manufacturing process is fast, low-cost, and completely compatible with the normal equipment used in MEMS foundries.

In addition, a CPAP device that includes a plurality of valves according to this disclosure may have small dimensions, be of low cost, and present high capacity for regulation and control of the flow of air supplied to the user.

Finally, it is clear that modifications and variations may be made to the embodiments described and illustrated herein, without thereby departing from the scope of the present disclosure.

For instance, it is possible to provide the inlet chamber 6 of dimensions such that a plurality of cantilever structures 4 extend over a same chamber 6.

Further, the stress-inducing layer 17 may extend only partially on the piezoelectric actuator 5, or else alongside it, or else, again, underneath the piezoelectric actuator 5.

According to a further embodiment, the stress-inducing layer 17 may be absent and the cantilever structure 4 may be kept substantially parallel to the plane XY by producing and biasing the piezoelectric actuator 5 so that it will generate a compressive stress within the cantilever structure 4 in the operating condition where the valve is closed.

The invention claimed is:

1. A valve module, comprising:
a semiconductor body including a plurality of cavities that are separated from each other by a distance;
wherein portions of the semiconductor body form a plurality of cantilever structures, each cantilever structure suspended over a respective cavity and being designed to move along one direction only when actuated, that direction corresponding to a positive bending of the cantilever structure away from the cavity, wherein each cantilever structure is spaced apart from a trench adjacent a distal end of that cantilever structure; and
a plurality of piezoelectric actuators, each of which partially covers one respective cantilever structure;
at least one voltage generator, operatively coupled to the plurality of piezoelectric actuators, configured to operate each piezoelectric actuator in a plurality of states, including at least:
a rest state, wherein a given piezoelectric actuator is not biased, in which a first non-zero air flow flows in through the respective cavity associated with that piezoelectric actuator and its cantilever structure and out through the trench; and
an actuated state, wherein the given piezoelectric actuator is biased such that its cantilever structure permits a second non-zero air flow in through the respective cavity associated with that piezoelectric actuator and its cantilever and out through the trench, the second non-zero air flow being greater than the first non-zero air flow.

2. The valve module according to claim 1, wherein the plurality of piezoelectric actuators comprise a first piezoelectric actuator and a second piezoelectric actuator, wherein the first and second piezoelectric actuators are coupled, respectively, to a first voltage generator and a second voltage generator so that the first and second piezoelectric actuators are controllable independently of one another.

3. The valve module according to claim 1, wherein each cantilever structure of the plurality of cantilever structures further comprises a stress-inducing layer that is configured to generate, in the cantilever structure, a compressive stress.

4. The valve module according to claim 1, wherein the plurality of cantilever structures number between 200 and 500.

5. The valve module according to claim 1, wherein each cantilever structure of the plurality of cantilever structures is mechanically constrained to the semiconductor body and seamlessly extends as a prolongation of the semiconductor body over the respective cavity.

6. The valve module according to claim 1, wherein each of the plurality of cavities is delimited internally by respective walls covered by a respective protective layer.

7. The valve module according to claim 1, wherein respective planarization layers extend underneath the piezoelectric actuators.

8. A respiratory aid device of a Continuous Positive Airway Pressure (CPAP) type comprising a plurality of valve modules according to claim 1.

9. A method for manufacturing a valve module, comprising:
    forming a plurality of cavities in a semiconductor body that are separated from each other by a distance;
    forming a plurality of cantilever structures, wherein each cantilever structure is suspended over a respective cavity and being designed to move along one direction only when actuated, that direction corresponding to a positive bending of the cantilever structure away from the cavity, wherein each cantilever structure is spaced apart from a trench adjacent a distal end of that cantilever structure; and
    coupling a piezoelectric actuator to each cantilever structure;
    operating each piezoelectric actuator in a plurality of states, including at least:
        a rest state, wherein a given piezoelectric actuator is not biased, in which a first non-zero air flow flows in through the respective cavity associated with that piezoelectric actuator and its cantilever structure and out through the trench; and
        an actuated state, wherein the given piezoelectric actuator is biased such that its cantilever structure permits a second non-zero air flow in through the respective cavity associated with that piezoelectric actuator and its cantilever and out through the trench, the second non-zero air flow being greater than the first non-zero air flow.

10. The method according to claim 9, further comprising forming respective conductive biasing paths for a first piezoelectric actuator and a second piezoelectric actuator so that each one of the first and second piezoelectric actuators is independently controllable.

11. The method according to claim 9, further comprising forming, on each cantilever structure, a stress-inducing layer configured to apply a compressive stress in each cantilever structure.

12. The method according to claim 9, wherein the plurality of cantilever structures number between 200 and 500.

13. The method according to claim 9, wherein forming the plurality of cantilever structures comprises, for each cantilever structure:
    forming a buried cavity in the semiconductor body;
    digging a trench that partially surrounds the cantilever structure until the buried cavity is reached; and
    keeping a portion of the cantilever structure constrained to the semiconductor body, as a seamless prolongation of the semiconductor body.

14. The method according to claim 9, wherein forming the respective cavity further comprises coating internal walls of the respective cavity with a protective layer.

15. The method according to claim 9, further comprising forming a planarization layer underneath the piezoelectric actuators.

16. A valve module adapted to receive at input a first air flow and supply at output a second air flow, comprising:
    a semiconductor body;
    a plurality of cavities in the semiconductor body at a distance from one another;
    a plurality of cantilever structures, each of which is suspended over a respective cavity and is designed to move along one direction only, corresponding to a positive bending of that cantilever structure away from its respective cavity;
    a plurality of piezoelectric actuators, each of which partially covers one respective cantilever structure;
    at least one voltage generator, operatively coupled to said plurality of piezoelectric actuators, to operate each piezoelectric actuator in a plurality of states, including:
        a rest state, wherein that piezoelectric actuator is not biased;
        an occlusion state, wherein that piezoelectric actuator is biased at a first voltage value for which its respective cantilever structure occludes the cavity inhibiting the second air flow;
        a fully-open state, wherein that piezoelectric actuator is biased at a second voltage value, higher than the first voltage value, such as to induce a tensile stress in its respective cantilever structure that causes said positive bending of that cantilever structure with a first entity, thus maximizing the flow rate of the second air flow; and
        an intermediate open state, wherein that piezoelectric actuator is biased at a third voltage value, between the first and the second voltage value, so as to induce a tensile stress in that cantilever structure that causes said positive bending of that cantilever structure of a second entity lower than the first entity, thus generating a corresponding intermediate flow rate of the second air flow lower than the maximum flow rate of the second air flow; and
    wherein each cantilever structure further comprises a stress-inducing layer, configured to generate, in that cantilever structure, a compressive stress designed as a function of a maximum pressure exerted, in use, by the first air flow on each respective cantilever structure, so that when that piezoelectric actuator is in the rest state, the first air flow does not cause positive bending of that cantilever structure exceeding a preset tolerance value, the positive bending of that cantilever structure allowing a non-zero flow rate of the first air flow.

17. The valve module according to claim 16, wherein two or more of said piezoelectric actuators include respective conductive biasing paths, coupled to respective voltage generators so that two or more of said piezoelectric actuators may be controlled independently of one another.

18. The valve module according to claim 16, wherein said plurality of cantilever structures numbers between 200 and 500.

19. The valve module according to claim 16, wherein each of said cantilever structures is mechanically constrained to the semiconductor body and extends as a prolongation of the latter seamlessly.

20. The valve module according to claim 16, wherein said cavities are delimited internally by respective walls covered by a respective protective layer.

21. The valve module according to claim 16, wherein respective planarization layers extend underneath said piezoelectric actuators.

22. The valve module according to claim 16, further comprising trenches, each trench partially surrounding a respective cantilever structure and reaching its respective cavity.

* * * * *